(12) United States Patent
Ludwin et al.

(10) Patent No.: US 10,307,205 B2
(45) Date of Patent: Jun. 4, 2019

(54) SYSTEM AND METHOD FOR DETECTION OF METAL DISTURBANCE BASED ON ORTHOGONAL FIELD COMPONENTS

(75) Inventors: Doron Moshe Ludwin, Haifa (IL); Meir Bar-Tal, Haifa (IL); Daniel Osadchy, Haifa (IL); Barak Pinkovich, Haifa (IL); Yevgeny Bonyak, Haifa (IL); Dror Levy, Qiryat Tivon (IL)

(73) Assignee: BIOSENSE WEBSTER (ISRAEL) LTD., Yokneam (IL)

( * ) Notice: Subject to any disclaimer, the term of this patent is extended or adjusted under 35 U.S.C. 154(b) by 400 days.

(21) Appl. No.: 12/965,245

(22) Filed: Dec. 10, 2010

(65) Prior Publication Data

US 2012/0149967 A1    Jun. 14, 2012

(51) Int. Cl.
| | | |
|---|---|---|
| *A61B 5/00* | (2006.01) | |
| *A61B 5/06* | (2006.01) | |
| *A61B 8/00* | (2006.01) | |
| *A61N 1/05* | (2006.01) | |
| *A61B 17/00* | (2006.01) | |

(Continued)

(52) U.S. Cl.
CPC ............ *A61B 18/1492* (2013.01); *A61B 5/06* (2013.01); *A61B 5/062* (2013.01); *A61B 5/6846* (2013.01); *A61B 8/445* (2013.01); *A61B 2017/00318* (2013.01); *A61B 2017/00876* (2013.01); *A61B 2018/00357* (2013.01);

(Continued)

(58) Field of Classification Search
CPC ....... A61B 6/527; A61B 12/5244; A61B 6/12; A61B 8/5269; A61B 5/721; A61B 8/12; A61B 8/445; A61B 18/1492; A61B 5/06; A61B 5/062; A61B 5/6846; A61B 2017/00318; A61B 2017/00876; A61B 2017/00357; A61B 2018/00589; A61N 1/065

USPC ................. 600/424; 606/33; 324/67, 442
See application file for complete search history.

(56) References Cited

U.S. PATENT DOCUMENTS

| | | | |
|---|---|---|---|
| 5,391,199 A | 2/1995 | Ben-Haim | |
| 6,147,480 A * | 11/2000 | Osadchy et al. | ................. 324/67 |

(Continued)

FOREIGN PATENT DOCUMENTS

| | | |
|---|---|---|
| CN | 101120877 A | 2/2008 |
| CN | 101129264 A | 2/2008 |

(Continued)

OTHER PUBLICATIONS

U.S. Appl. No. 11/868,733, filed Oct. 8, 2007—pending.

(Continued)

*Primary Examiner* — Jennifer Dieterle
*Assistant Examiner* — Helene Bor
(74) *Attorney, Agent, or Firm* — Notaro, Michalos & Zaccaria P.C.

(57) ABSTRACT

Apparatus and method for detecting metal disturbance during a medical procedure includes a probe having an insertion tube, a joint and a joint sensor, contained within the probe, for sensing a position of the insertion tube. The joint sensor has first and second subassemblies that are magnetic transducers. A processor is used for measuring force using the joint sensor, and has a threshold field value stored therein. The processor compares a sensed field value to the threshold field value and identifies a presence metal when the sensed field value is greater than the threshold field value.

16 Claims, 6 Drawing Sheets

(51) Int. Cl.
*A61B 18/00* (2006.01)
*A61B 18/14* (2006.01)
*A61B 90/00* (2016.01)

(52) U.S. Cl.
CPC .............. *A61B 2018/00589* (2013.01); *A61B 2090/0811* (2016.02); *A61N 1/056* (2013.01)

(56) References Cited

U.S. PATENT DOCUMENTS

| | | | |
|---|---|---|---|
| 6,172,499 | B1 | 1/2001 | Ashe |
| 6,239,724 | B1 | 5/2001 | Doron et al. |
| 6,272,371 | B1 * | 8/2001 | Shlomo .................. 600/424 |
| 6,332,089 | B1 | 12/2001 | Acker et al. |
| 6,484,118 | B1 | 11/2002 | Govari |
| 6,618,612 | B1 | 9/2003 | Acker et al. |
| 6,690,963 | B2 | 2/2004 | Ben-Haim et al. |
| 7,397,364 | B2 | 7/2008 | Govari |
| 7,545,140 | B2 | 6/2009 | Humphreys et al. |
| 7,688,064 | B2 * | 3/2010 | Shalgi et al. ............ 324/207.12 |
| 8,082,020 | B2 * | 12/2011 | Bar-Tal et al. ............... 600/424 |
| 8,083,691 | B2 | 12/2011 | Goldenberg et al. |
| 2002/0065455 | A1 * | 5/2002 | Ben-Haim ......... A61N 1/36564 600/407 |
| 2003/0120150 | A1 | 6/2003 | Govari |
| 2004/0059328 | A1 | 3/2004 | Daniel et al. |
| 2004/0068178 | A1 | 4/2004 | Govari |
| 2005/0024043 | A1 | 2/2005 | Govari |
| 2006/0200049 | A1 | 9/2006 | Leo et al. |
| 2007/0021742 | A1 | 1/2007 | Viswanathan |
| 2007/0093798 | A1 | 4/2007 | DeBenedictis et al. |
| 2007/0100332 | A1 | 5/2007 | Paul et al. |
| 2008/0012553 | A1 * | 1/2008 | Shalgi et al. ............ 324/207.17 |
| 2008/0054893 | A1 * | 3/2008 | Humphreys ........... G01V 3/107 324/239 |
| 2009/0082665 | A1 | 3/2009 | Anderson |
| 2009/0138007 | A1 * | 5/2009 | Govari et al. .................. 606/33 |
| 2010/0069921 | A1 * | 3/2010 | Miller ................ A61B 18/1233 606/130 |
| 2011/0153252 | A1 | 6/2011 | Govari et al. |

FOREIGN PATENT DOCUMENTS

| | | |
|---|---|---|
| CN | 101416874 A | 4/2009 |
| CN | 101584583 A | 11/2009 |
| CN | 101780303 A | 7/2010 |
| EP | 1 174 082 A1 | 1/2002 |
| EP | 1 400 216 A1 | 3/2004 |
| EP | 1 421 900 A1 | 5/2004 |
| EP | 1 743 574 A1 | 1/2007 |
| EP | 1 767 166 A1 | 3/2007 |
| EP | 2 026 175 A1 | 2/2009 |
| EP | 2 047 797 A2 | 4/2009 |
| EP | 2 332 461 A1 | 6/2011 |
| EP | 2 338 412 A1 | 6/2011 |
| JP | 2003-530557 | 10/2001 |
| JP | 2005-052645 A | 3/2005 |
| JP | 2008-86751 | 4/2008 |
| JP | 2009-291616 A | 12/2009 |
| JP | 2010-57911 | 3/2010 |
| JP | 2010-131390 | 6/2010 |
| WO | WO 96/05768 A1 | 2/1996 |
| WO | WO 2001/77701 A1 | 10/2001 |

OTHER PUBLICATIONS

U.S. Appl. No. 12/134,592, filed Jun. 6, 2008—pending.
U.S. Appl. No. 12/327,226, filed Dec. 3, 2008—pending.
Extended European Search Report dated Feb. 22, 2012 from related European Application No. 11192888.3.
Chinese Office Action dated Sep. 11, 2014 from related Chinese Application No. 201110429188.8, together with an English language translation.
United States Office Action dated Jul. 9, 2014 received in related U.S. Appl. No. 12/965,267.
United States Office Action dated Dec. 18, 2013 received in related U.S. Appl. No. 12/965,267.
European Official Action dated Mar. 19, 2013 received in related EP 11 192 844.6.
United States Office Action dated Oct. 16, 2014 received in related U.S. Appl. No. 12/965,201.
Extended European Search Report dated Apr. 17, 2012 received in related EP 11 192 744.8.
Chinese Office Action dated Aug. 27, 2014 from related Chinese Application No. 201110429134.1, together with an English language translation.
United States Notice of Allowance dated Jan. 29, 2015 received in related U.S. Appl. No. 12/965,267.
United States Office Action dated Feb. 9, 2015 received in related U.S. Appl. No. 12/965,201.
Chinese Official Action dated Jan. 6, 2015 received in related application CN 201110429186.9 together with an English language translation.
Japanese Office Action dated Jul. 14, 2015 from related Japanese Application No. 2011-269953, together with an English language translations.
Japanese Office Action dated Jan. 8, 2016 from Japanese Application No. No. 2011-269978, together with an English language translations.
Official Action for Canadian Application No. 2,759,626 dated Oct. 2, 2017.

* cited by examiner

SYSTEM AND METHOD FOR DETECTION OF METAL DISTURBANCE BASED ON ORTHOGONAL FIELD COMPONENTS

FIELD OF THE INVENTION

The present invention relates generally to invasive medical devices capable of sensing displacement of a joint in a probe, such as a catheter that is applied to the body of a patient, and more specifically to a system and method for using such a catheter that is capable of detecting the presence metal objects located anywhere near the catheter as well as for accounting and/or correcting for the presence of such metal object.

BACKGROUND OF THE INVENTION

In some diagnostic and therapeutic techniques, a catheter is inserted into a chamber of the heart and brought into contact with the inner heart wall. In such procedures, it is generally important that the distal tip of the catheter engages the endocardium with sufficient pressure to ensure good contact. Excessive pressure, however, may cause undesired damage to the heart tissue and even perforation of the heart wall.

For example, in intracardiac radio-frequency (RF) ablation, a catheter having an electrode at its distal tip is inserted through the patient's vascular system into a chamber of the heart. The electrode is brought into contact with a site (or sites) on the endocardium, and RF energy is applied through the catheter to the electrode in order to ablate the heart tissue at the site. Proper contact between the electrode and the endocardium during ablation is necessary in order to achieve the desired therapeutic effect without excessive damage to the tissue.

A number of patent publications describe catheters with integrated pressure sensors for sensing tissue contact. As one example, U.S. Patent Application Publication 2007/0100332, whose disclosure is incorporated herein by reference, describes systems and methods for assessing electrode-tissue contact for tissue ablation. An electromechanical sensor within the catheter shaft generates electrical signals corresponding to the amount of movement of the electrode within a distal portion of the catheter shaft. An output device receives the electrical signals for assessing a level of contact between the electrode and a tissue.

To date, there have been no prior art systems and methods that are capable of determining accurate position information and force measurements for a medical device that is used within a body of a patient while being able to detect field distortion caused by metal interference from a metal object located near the device with the ability to account for and correct its force readings/measurements and/or its position information.

SUMMARY OF THE INVENTION

The present invention is directed to an apparatus for detecting metal disturbance during a medical procedure comprising a probe, which comprises an insertion tube, having a longitudinal axis and having a distal end and a distal tip, which is disposed at the distal end of the insertion tube and is configured to be brought into contact with tissue of the body. A joint, which couples the distal tip to the distal end of the insertion tube is used in conjunction with a joint sensor, contained within the probe, for sensing a position of the distal tip relative to the distal end of the insertion tube. The joint sensor comprises first and second subassemblies, which are disposed within the probe on opposite, respective sides of the joint and each comprise one or more magnetic transducers.

Apparatus also comprises a processor for determining a force measurement using the joint sensor, and having a threshold field value stored therein, and which is coupled to apply a current to one of the first and second subassemblies, thereby causing the one of the subassemblies to generate at least one magnetic field. The processor is coupled to receive and process one or more signals output by the other of the first and second subassemblies responsively to the at least one magnetic field so as to detect changes in a position of the distal tip relative to the distal end of the insertion tube, wherein the one or more signals output by the other of the first and second subassemblies define a sensed field value.

The processor compares the sensed field value to the threshold field value and identifies a presence of a metal object near a distal end of the probe when the sensed field value is below the threshold field value. In many instances, the sensed field value is based on a field in the axial direction.

The present invention is also directed to a method for detecting metal disturbance during a medical procedure performed on a body of a patient comprising the steps of providing a probe, which comprises an insertion tube, having a longitudinal axis and having a distal end, a distal tip, which is disposed at the distal end of the insertion tube and is configured to be brought into contact with tissue of the body, and a joint, which couples the distal tip to the distal end of the insertion tube, and a joint sensor, contained within the probe, for sensing a position of the distal tip relative to the distal end of the insertion tube. The joint sensor comprises first and second subassemblies, which are disposed within the probe on opposite, respective sides of the joint and each comprise one or more magnetic transducers.

A processor is used for determining a force measurement using the joint sensor and having a threshold field value stored therein. A current is applied to one of the first and second subassemblies, thereby causing the one of the subassemblies to generate at least one magnetic field wherein the at least one magnetic field at the other of the first and second subassemblies is received and one or more signals by the other of the first and second subassemblies is output responsively to the at least one magnetic field, wherein the one or more signals output by the other of the first and second subassemblies define a sensed field value.

Changes in a position of the distal tip relative to the distal end of the insertion tube are detected and the processor compares the sensed field value to the threshold field value and identifies a presence of a metal object near a distal end of the probe when the sensed field value is below the threshold field value. In many instances, the sensed field value is based on a field in the axial direction.

In another embodiment, the present invention is directed to apparatus for detecting metal disturbance during a medical procedure comprising a probe, which comprises an insertion tube, having a longitudinal axis and having a distal end and a distal tip, which is disposed at the distal end of the insertion tube and is configured to be brought into contact with tissue of the body. The probe also has a joint, which couples the distal tip to the distal end of the insertion tube; and a joint sensor, contained within the probe, for sensing a position of the distal tip relative to the distal end of the insertion tube. The joint sensor comprises first and second subassemblies, which are disposed within the probe on opposite, respective sides of the joint and each comprise one or more magnetic transducers.

A processor is used for determining a force measurement using the joint sensor, and having a pre-established baseline value stored therein, and which is coupled to apply a current to one of the first and second subassemblies, thereby causing the one of the subassemblies to generate at least one magnetic field.

The processor is coupled to receive and process one or more signals output by the other of the first and second subassemblies responsively to the at least one magnetic field so as to detect changes in a position of the distal tip relative to the distal end of the insertion tube.

The magnetic transducers comprise coils, and wherein the first subassembly comprises a first coil having a first coil axis parallel to the longitudinal axis of the insertion tube, and wherein the second subassembly comprises two or more other coils in different, respective radial locations within a section of the probe that is spaced apart axially from the first subassembly.

The processor applies current to one coil of the two or more other coils of the second subassembly and measures a signal output by a remainder of the two or more other coils of the second subassembly. The signal output by a remainder of the two or more other coils of the second subassembly defines a pickup value, wherein the processor compares the pickup value to the pre-established baseline value and identifies a presence of a metal object near a distal end of the probe when the pickup value is outside of a range of the pre-established baseline value. In many instances, the pickup value is based on mutual inductance measured from the remainder of the two or more other coils of the second subassembly.

The present invention is also directed to a method for detecting metal disturbance during a medical procedure performed on a body of a patient comprising the steps of providing a probe, which comprises an insertion tube, having a longitudinal axis and having a distal end, a distal tip, which is disposed at the distal end of the insertion tube and is configured to be brought into contact with tissue of the body, a joint, which couples the distal tip to the distal end of the insertion tube, and a joint sensor, contained within the probe, for sensing a position of the distal tip relative to the distal end of the insertion tube.

The joint sensor comprises first and second subassemblies, which are disposed within the probe on opposite, respective sides of the joint and each comprise one or more magnetic transducers, and a processor for determining a force measurement using the joint sensor. The processor has a pre-established baseline value stored therein, and which is coupled to apply a current to one of the first and second subassemblies, thereby causing the one of the subassemblies to generate at least one magnetic field, and which is coupled to receive and process one or more signals output by the other of the first and second subassemblies responsively to the at least one magnetic field so as to detect changes in a position of the distal tip relative to the distal end of the insertion tube.

The magnetic transducers comprise coils, and wherein the first subassembly comprises a first coil having a first coil axis parallel to the longitudinal axis of the insertion tube, and wherein the second subassembly comprises two or more other coils in different, respective radial locations within a section of the probe that is spaced apart axially from the first subassembly.

Current is then applied to one coil of the two or more other coils of the second subassembly a signal output is measured by a remainder of the two or more other coils of the second subassembly, wherein the signal output by a remainder of the two or more other coils of the second subassembly define a pickup value. The pickup value is then compared to the pre-established baseline value and a presence of a metal object near a distal end of the probe is identified when the pickup value is outside of a range of the pre-established baseline value. In many instances, mutual inductance is measured from the remainder of the two or more other coils of the second subassembly for determining the pickup value.

In yet another embodiment according to the present invention, the present invention is directed to apparatus for detecting metal disturbance during a medical procedure comprising a probe, which comprises an insertion tube, having a longitudinal axis and having a distal end and a distal tip, which is disposed at the distal end of the insertion tube and is configured to be brought into contact with tissue of the body. The probe also comprises a joint, which couples the distal tip to the distal end of the insertion tube; and a joint sensor, contained within the probe, for sensing a position of the distal tip relative to the distal end of the insertion tube. The joint sensor comprises first and second subassemblies, which are disposed within the probe on opposite, respective sides of the joint and each comprise one or more magnetic transducers.

A processor is used for determining a force measurement using the joint sensor, and having a threshold field value stored therein. The processor is coupled to apply a current to one of the first and second subassemblies, thereby causing the one of the subassemblies to generate at least one magnetic field, and which is coupled to receive and process one or more signals output by the other of the first and second subassemblies responsively to the at least one magnetic field so as to detect changes in a position of the distal tip relative to the distal end of the insertion tube, wherein the one or more signals output by the other of the first and second subassemblies define a sensed field value. The processor compares the sensed field value to the threshold field value and identifies a presence of a metal object near a distal end of the probe when the sensed field value is greater than the threshold field value. In many cases, the sensed field value is based on a field in the radial or orthogonal direction.

The present invention is also directed to a method for detecting metal disturbance during a medical procedure performed on a body of a patient comprising the steps of providing a probe, which comprises an insertion tube, having a longitudinal axis and having a distal end, a distal tip, which is disposed at the distal end of the insertion tube and is configured to be brought into contact with tissue of the body, and a joint, which couples the distal tip to the distal end of the insertion tube, and a joint sensor, contained within the probe, for sensing a position of the distal tip relative to the distal end of the insertion tube.

The joint sensor comprises first and second subassemblies, which are disposed within the probe on opposite, respective sides of the joint and each comprise one or more magnetic transducers. A processor is used for determining a force measurement using the joint sensor and having a threshold field value stored therein.

Current is then applied to one of the first and second subassemblies, thereby causing the one of the subassemblies to generate at least one magnetic field. The at least one magnetic field is received at the other of the first and second subassemblies and one or more signals by the other of the first and second subassemblies is output responsively to the at least one magnetic field, wherein the one or more signals output by the other of the first and second subassemblies define a sensed field value.

Changes are detected in a position of the distal tip relative to the distal end of the insertion tube and the sensed field value is compared to the threshold field value; and a presence of a metal object near a distal end of the probe is identified when the sensed field value is greater than the threshold field value. In many cases, the sensed field value is based on a field in the radial or orthogonal direction.

The present invention will be more fully understood from the following detailed description of the embodiments thereof, taken together with the drawings in which:

DETAILED DESCRIPTION OF THE INVENTION

Figure 1:
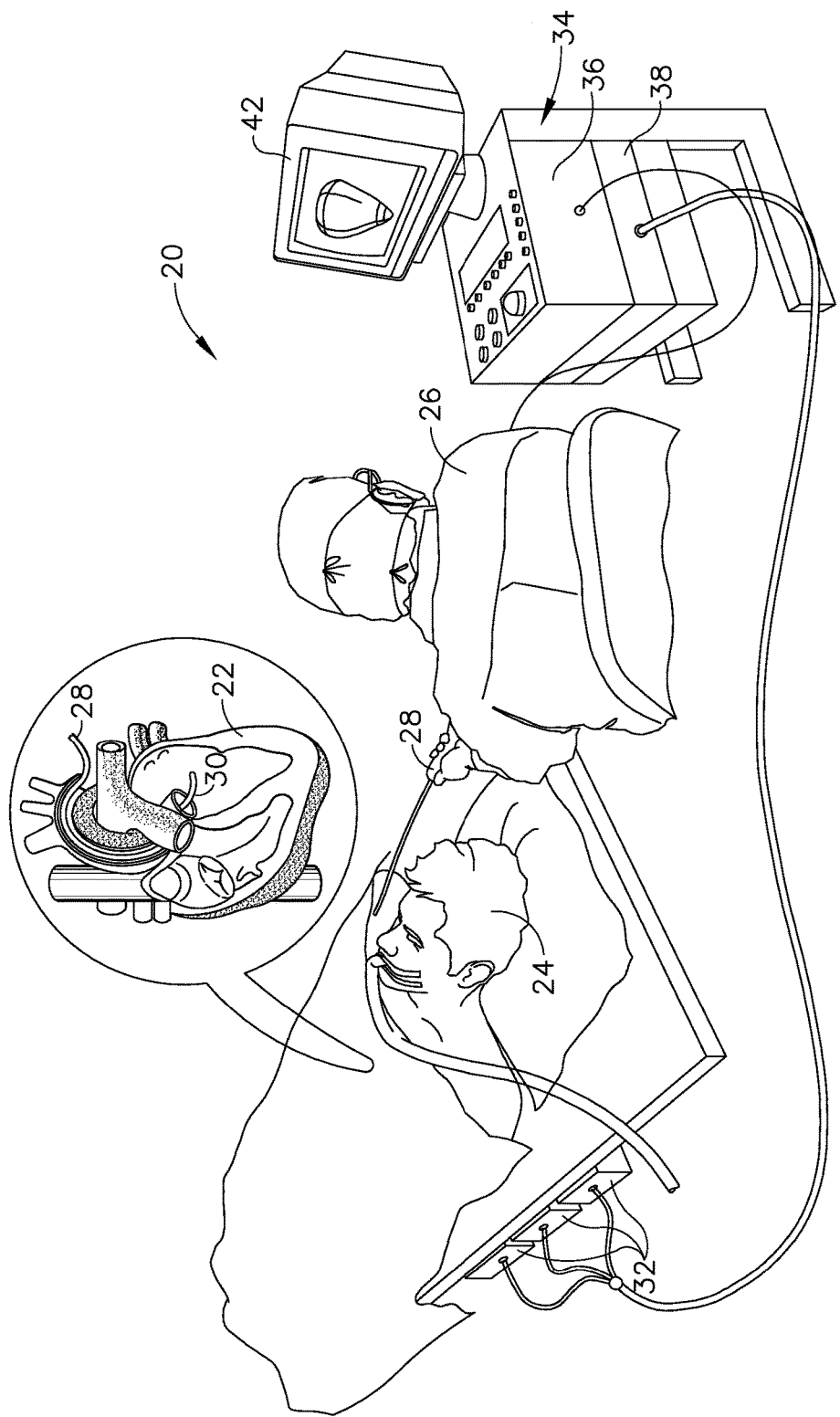
FIG. 1 is a schematic, pictorial illustration of a catheter-based medical system, in accordance with an embodiment of the present invention.

This application uses the technical disclosure of commonly owned pending U.S. patent application Ser. No. 11/868,733, filed Oct. 8, 2007, and U.S. patent application Ser. No. 12/327,226, filed Dec. 3, 2008 which are assigned to the assignee of the present patent application and whose disclosure of both references is incorporated herein by reference. Accordingly, like or similar features are identified using the same reference numerals from U.S. patent application Ser. No. 12/327,226.

The above-mentioned U.S. patent application Ser. No. 11/868,733 describes a catheter whose distal tip is coupled to the distal end of the catheter insertion tube by a spring-loaded joint, which deforms in response to pressure exerted on the distal tip when it engages tissue. A magnetic position sensing assembly within the probe, comprising coils on opposite sides of the joint, senses the position of the distal tip relative to the distal end of the insertion tube. Changes in this relative position are indicative of deformation of the spring and thus give an indication of the pressure.

Embodiments of the present invention that are described herein below utilize the new design of the sensing assembly of U.S. patent application Ser. No. 12/327,226, which facilitates more precise measurement of tip movement and ultimately facilitates the detection of a metallic object located near the catheter. The configuration of the coils in this design permits precise sensing of very small deflections and compressions of the joint connecting the catheter tip to the insertion tube. Therefore, the pressure on the tip can be measured with enhanced accuracy, permitting the use a relatively stiffer spring in the catheter, which makes the catheter more reliable and easier to maneuver in the body. Moreover, operation of these coils on the catheter allow for the detection of metal objects located anywhere near catheter.

Preferred embodiments according to the present invention as further described in detail later on in this disclosure are directed to a system and method for using such a catheter that is capable of detecting the presence metal objects located anywhere near the catheter as well as for accounting and/or correcting for the presence of such metal object.

FIG. 1 is a schematic, pictorial illustration of a system 20 for cardiac catheterization, in accordance with an embodiment of the present invention. System 20 may be based, for example, on the CARTO™ system, produced by Biosense Webster Inc. (Diamond Bar, Calif.). This system comprises an invasive probe in the form of a catheter 28 and a control console 34. In the embodiment described hereinbelow, it is assumed that catheter 28 is used in ablating endocardial tissue, as is known in the art. Alternatively, the catheter may be used, mutatis mutandis, for other therapeutic and/or diagnostic purposes in the heart or in other body organs.

An operator 26, such as a cardiologist, inserts catheter 28 through the vascular system of a patient 24 so that a distal end 30 of the catheter enters a chamber of the patient's heart 22. The operator advances the catheter so that the distal tip of the catheter engages endocardial tissue at a desired location or locations. Catheter 28 is typically connected by a suitable connector at its proximal end to console 34. The console may comprise a radio frequency (RF) generator, which supplies high-frequency electrical energy via the catheter for ablating tissue in the heart at the locations engaged by the distal tip. Alternatively or additionally, the catheter and system may be configured to perform other therapeutic and diagnostic procedures that are known in the art.

Console 34 uses magnetic position sensing to determine position coordinates of distal end 30 of catheter 28 inside heart 22. For this purpose, a driver circuit 38 in console 34 drives field generators 32 to generate magnetic fields in the vicinity of the body of patient 24. Typically, the field generators comprise coils, which are placed below the patient's torso at known positions external to the patient. These coils generate magnetic fields within the body in a predefined working volume that contains heart 22. A magnetic field sensor within distal end 30 of catheter 28 (shown in FIG. 3) generates electrical signals in response to these magnetic fields. A signal processor 36 processes these signals in order to determine the position coordinates of the distal end, typically including both location and orientation coordinates. This method of position sensing is implemented in the above-mentioned CARTO system and is described in detail in U.S. Pat. Nos. 5,391,199, 6,690,963, 6,484,118, 6,239,724, 6,618,612 and 6,332,089, in PCT Patent Publication WO 96/05768, and in U.S. Patent Application Publications 2002/0065455 A1, 2003/0120150 A1 and 2004/0068178 A1, whose disclosures are all incorporated herein by reference.

Processor 36 typically comprises a general-purpose computer, with suitable front end and interface circuits for receiving signals from catheter 28 and controlling the other components of console 34. The processor may be programmed in software to carry out the functions that are described herein. The software may be downloaded to console 34 in electronic form, over a network, for example, or it may be provided on tangible media, such as optical, magnetic or electronic memory media. Alternatively, some or all of the functions of processor may be carried out by dedicated or programmable digital hardware components. Based on the signals received from the catheter and other components of system 20, processor 36 drives a display 42 to give operator 26 visual feedback regarding the position of distal end 30 in the patient's body, as well as regarding displacement of the distal tip of the catheter, and status information and guidance regarding the procedure that is in progress.

Alternatively or additionally, system 20 may comprise an automated mechanism for maneuvering and operating catheter 28 within the body of patient 24. Such mechanisms are typically capable of controlling both the longitudinal motion (advance/retract) of the catheter and transverse motion (deflection/steering) of the distal end of the catheter. Some mechanisms of this sort use DC magnetic fields for this purpose, for example. In such embodiments, processor 36 generates a control input for controlling the motion of the catheter based on the signals provided by the magnetic field sensor in the catheter. These signals are indicative of both the position of the distal end of the catheter and of force exerted on the distal end, as explained further hereinbelow.

Figure 2:
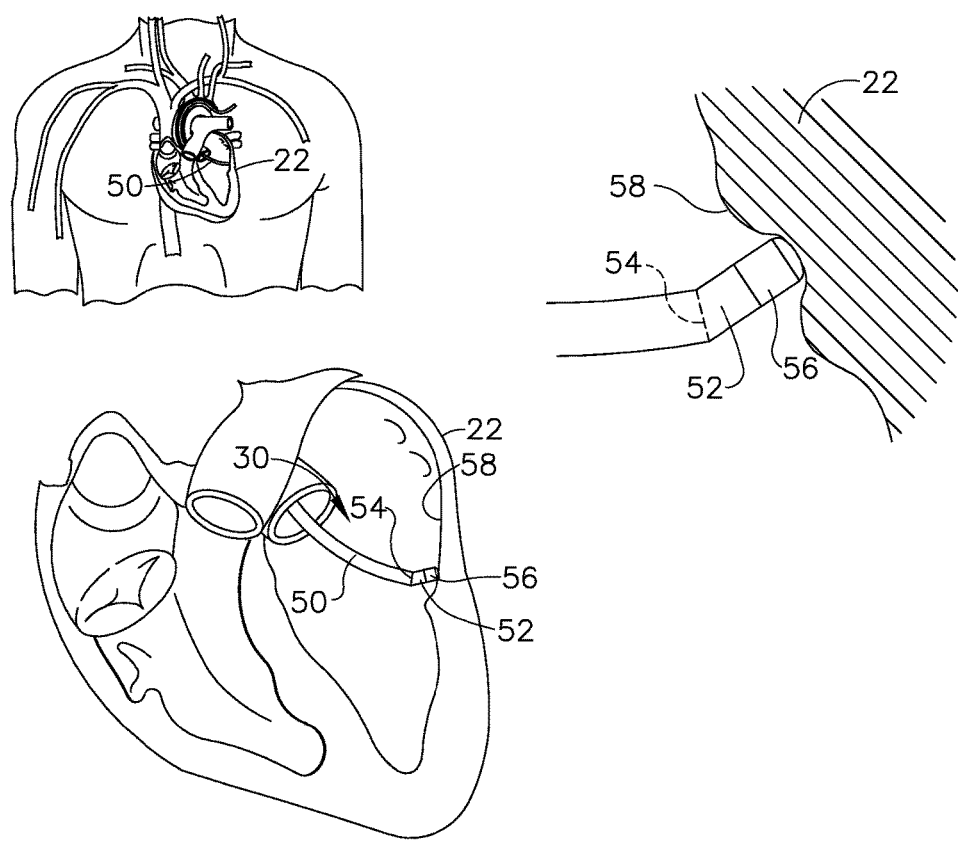
FIG. 2 is a schematic detail view showing the distal tip of a catheter in contact with endocardial tissue, in accordance with an embodiment of the present invention.

FIG. 2 is a schematic sectional view of a chamber of a heart 22, showing distal end 30 of catheter 28 inside the heart, in accordance with an embodiment of the present invention. The catheter comprises an insertion tube 50, which is typically inserted into the heart percutaneously through a blood vessel, such as the vena cava or the aorta. An electrode 56 on a distal tip 52 of the catheter engages endocardial tissue 58. Pressure exerted by the distal tip against the endocardium deforms the endocardial tissue locally, so that electrode 56 contacts the tissue over a relatively large area. In the pictured example, the electrode engages the endocardium at an angle, rather than head-on. Distal tip 52 therefore bends at an elastic joint 54 relative to the distal end of insertion tube 50 of the catheter. The bend facilitates optimal contact between the electrode and the endocardial tissue.

Because of the elastic quality of joint 54, the angle of bending and the axial displacement of the joint are proportional to the pressure exerted by tissue 58 on distal tip 52 (or equivalently, the pressure exerted by the distal tip on the tissue). Measurement of the bend angle and axial displacement thus gives an indication of this pressure. The pressure indication may be used by the operator of catheter 20 is ensuring that the distal tip is pressing against the endocardium firmly enough to give the desired therapeutic or diagnostic result, but not so hard as to cause undesired tissue damage.

Figure 3:
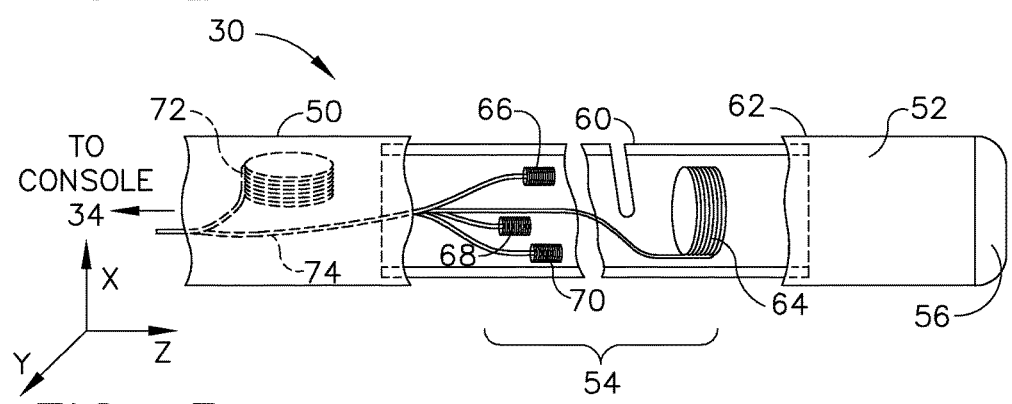
FIG. 3 is a schematic, sectional view showing details of the distal end of a catheter, in accordance with an embodiment of the present invention.

FIG. 3 is a schematic, sectional view of distal end 30 of catheter 28, showing details of the structure of the catheter in accordance with an embodiment of the present invention. Insertion tube 50 is connected to distal tip 52 by joint 54, as noted above. The insertion tube is covered by a flexible, insulating material 62, such as Celcon®, Teflon®, or heat-resistant polyurethane, for example. The area of joint 54 is covered, as well, by a flexible, insulating material, which may be the same as material 62 or may be specially adapted to permit unimpeded bending and compression of the joint. (This material is cut away in FIG. 3 in order to expose the internal structure of the catheter.) Distal tip 52 may be covered, at least in part, by electrode 56, which is typically made of a conductive material, such as a platinum/iridium alloy. Alternatively, other suitable materials may be used, as will be apparent to those skilled in the art. Further alternatively, for some applications, the distal tip may be made without a covering electrode. The distal tip is typically relatively rigid, by comparison with the flexible insertion tube.

Joint 54 comprises a resilient coupling member 60. In this embodiment, the coupling member has the form of a tubular piece of an elastic material, with a helical cut along a portion of its length. For example, the coupling member may comprise a superelastic alloy, such as nickel titanium (Nitinol). The helical cut causes the tubular piece to behave like a spring in response to forces exerted on distal tip 52. Further details regarding the fabrication and characteristics of this sort of coupling member are presented in U.S. patent application Ser. No. 12/134,592, filed Jun. 6, 2008, which is assigned to the assignee of the present patent application and whose disclosure is incorporated herein by reference. Alternatively, the coupling member may comprise a coil spring or any other suitable sort of resilient component with the desired flexibility and strength characteristics.

The stiffness of coupling member 60 determines the range of relative movement between tip 52 and insertion tube 50 in response to forces exerted on the distal tip. Such forces are encountered when the distal tip is pressed against the endocardium during an ablation procedure. The desired pressure for good electrical contact between the distal tip and the endocardium during ablation is on the order of 20-30 grams. The coupling member is configured to permit axial displacement (i.e., lateral movement along the axis of catheter 28) and angular deflection of the distal tip in proportion to the pressure on the tip. Measurement of the displacement and deflection by processor 36 gives an indication of the pressure and thus helps to ensure that the correct pressure is applied during ablation.

A joint sensing assembly, comprising coils 64, 66, 68 and 70 within catheter 28, provides accurate reading of the position of distal tip 52 relative to the distal end of insertion tube 50, including axial displacement and angular deflection. These coils are one type of magnetic transducer that may be used in embodiments of the present invention. A "magnetic transducer," in the context of the present patent application and in the claims, means a device that generates a magnetic field in response to an applied electrical current and/or outputs an electrical signal in response to an applied magnetic field. Although the embodiments described herein use coils as magnetic transducers, other types of magnetic transducers may be used in alternative embodiments, as will be apparent to those skilled in the art.

The coils in catheter 28 are divided between two subassemblies on opposite sides of joint 54: One subassembly comprises coil 64, which is driven by a current via a cable 74 from console 34 to generate a magnetic field. This field is received by a second subassembly, comprising coils 66, 68 and 70, which are located in a section of the catheter that is spaced axially apart from coil 64. (The term "axial," as used in the context of the present patent application and in the claims, refers to the direction of the longitudinal axis of distal end 30 of catheter 28, which is identified as the Z-direction in FIG. 3. An axial plane is a plane perpendicular to this longitudinal axis, and an axial section is a portion of the catheter contained between two axial planes.) Coils 66, 68 and 70 emit electrical signals in response to the magnetic field generated by coil 64. These signals are conveyed by cable 74 to processor 36, which processes the signals in order to measure the axial displacement and angular deflection of joint 54.

Coils 66, 68 and 70 are fixed in catheter 28 at different radial locations. (The term "radial" refers to coordinates relative to the catheter axis, i.e., coordinates in an X-Y plane in FIG. 3.) Specifically, in this embodiment, coils 66, 68 and 70 are all located in the same axial plane at different azimuthal angles about the catheter axis. For example, the three coils may be spaced azimuthally 120° apart at the same radial distance from the axis.

The axes of coils 64, 66, 68 and 70 are parallel to the catheter axis (and thus to one another, as long as joint 54 is undeflected). Consequently, coils 66, 68 and 70 will output strong signals in response to the field generated by coil 64, and the signals will vary strongly with the distances of coils 66, 68 and 70 from coil 64. (Alternatively, the axis of coil 64 and/or coils 66, 68 and 70 may be angled relative to the catheter axis, as long as the coil axes have a sufficient parallel component in order to give substantial signals). Angular deflection of tip 52 will give rise to a differential change in the signals output by coils 66, 68 and 70, depending on the direction and magnitude of deflection, since one or two of these coils will move relatively closer to coil 64. Compressive displacement of the tip will give rise to an increase in the signals from all of coils 66, 68 and 70.

Processor 36 analyzes the signals output by coils 66, 68 and 70 in order to measure the deflection and displacement of joint 54. The sum of the changes in the signals gives a measure of the compression, while the difference of the changes gives the deflection. The vector direction of the difference gives an indication of the bend direction. A suitable calibration procedure may be used to measure the precise dependence of the signals on deflection and displacement of the joint.

Various other configurations of the coils in the sensing subassemblies may also be used, in addition to the configuration shown and described above. For example, the positions of the subassemblies may be reversed, so that field generator coil is on the proximal side of joint 54, and the sensor coils are in the distal tip. As another alternative, coils 66, 68 and 70 may be driven as field generators (using time- and/or frequency-multiplexing to distinguish the fields), while coil 64 serves as the sensor. The sizes and numbers of the coils in FIG. 3 are shown only by way of example, and larger or smaller numbers of coils may similarly be used, in various different positions, so long as one of the subassemblies comprises at least two coils, in different radial positions, to allow differential measurement of joint deflection.

Prior calibration of the relation between pressure on tip 52 and movement of joint 54 may be used by processor 36 in translating the coil signals into terms of pressure. By virtue of the combined sensing of displacement and deflection, this pressure sensing system reads the pressure correctly regardless of whether the electrode engages the endocardium head-on or at an angle. The pressure reading is insensitive to temperature variations and free of drift, unlike piezoelectric sensors, for example. Because of the high sensitivity to joint motion that is afforded by the arrangement of coils 64, 66, 68 and 70 that is shown in FIG. 3, processor 36 can measure small displacements and deflections with high precision. Therefore, coupling member 60 can be made relatively stiff, and processor 36 will still be able to sense and measure accurately the pressure on tip 52. The stiffness of the coupling member makes it easier for the operator to maneuver and control the catheter.

Figure 4:
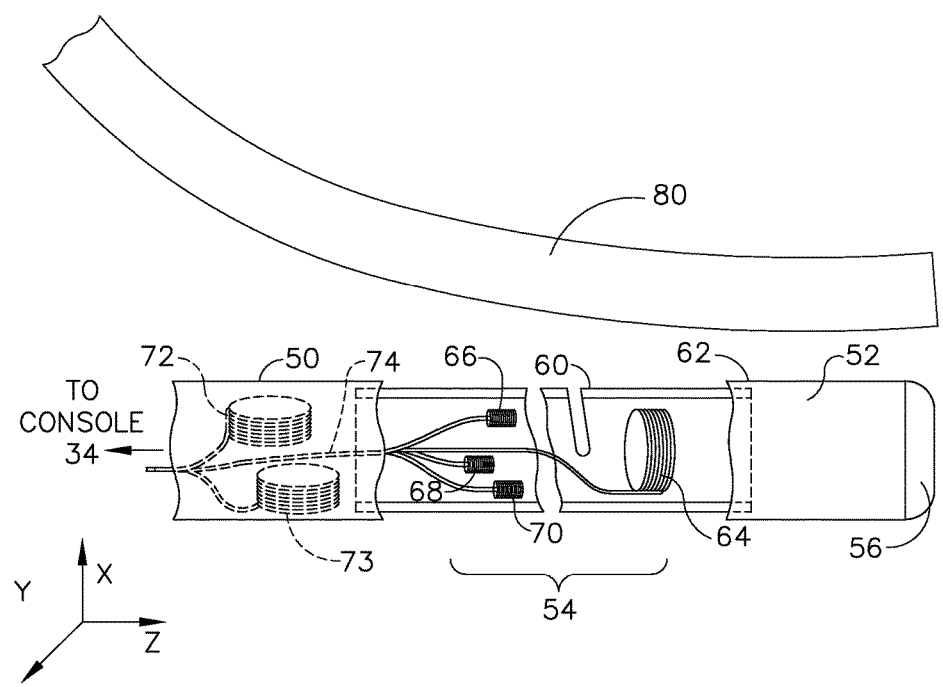
FIG. 4 is a schematic, sectional view showing details of the distal end of a catheter, in accordance with another embodiment of the present invention, in the presence of a metal object.

One or more of coils 64, 66, 68 and 70 may also be used to output signals in response to the magnetic fields generated by field generators 32, and thus serve as position sensing coils. Processor 36 processes these signals in order to determine the coordinates (position and orientation) of distal end 30 in the external frame of reference that is defined by the field generators. Additionally or alternatively, one or more further coils 72 and 73 (or other magnetic sensors) may be deployed in the distal end of the catheter for this purpose as best illustrated in FIG. 4. The position sensing coils in distal end 30 of catheter 28 enable console 34 to output both the location and orientation of the catheter in the body and the displacement and deflection of tip 52, as well as the pressure on the tip.

Although the operation of a magnetic position sensing assembly and its use in sensing pressure are described above in the context of catheter-based ablation, the principles of the present invention may similarly be applied in other applications that require accurate sensing of the movement of a joint, and particularly in therapeutic and diagnostic applications that use invasive probes, both in the heart and in other organs of the body. As one example, the devices and techniques for position and pressure sensing that are implemented in system 20 may be applied, mutatis mutandis, in guiding and controlling the use of a catheter insertion sheath. If the position of the sheath is not properly controlled and excessive force is used in its insertion, the sheath may perforate the heart wall or vascular tissue. This eventuality can be avoided by sensing the position of and pressure on the distal tip of the sheath. In this regard, the term "distal tip" as used herein should be understood to include any sort of structure at the distal end of a probe that may be bent and/or displaced relative to the main body of the probe.

One drawback for the technology described above is the presence of ferromagnetic material (metallic material) 80 located close to distal end and coils 64, 66, 68, 70, 72 of catheter 28 as best illustrated in FIG. 4. Such material may cause a distortion in the magnetic field and therefore may change the force readings. This distortion cannot be identified by looking at the force raw data alone, since this data is valid and acts as legitimate force readings, i.e. any three readings from the contact force sensors (coils) in joint 54 (even distorted) are directly mapped to a relevant force. The interference is noticeable when another metal containing device 80 comes in close proximity to distal tip 52 and joint 54 as show in FIG. 4.

This phenomenon is referred to as shaft proximity interference (SPI). The present invention is directed to novel apparatus and methods that provide a mechanism which enables the ability to distinguish between legitimate force readings and a force reading caused by a SPI.

As best illustrated in FIG. 4, the arrangement of coils 64, 66, 68, 70, 72 and 73 in catheter tip 52 enables sensitive measurement of the catheter bend angle and contact force experienced by catheter tip 52. This arrangement serves as the joint sensing assembly, comprising coils 64, 66, 68, 70, 72 and 73 which provides accurate reading of the position/location (in the form of position and orientation coordinate information in X,Y, and Z axis directions and yaw, pitch and roll orientations) of distal tip 52 relative to the distal end of insertion tube 50. Transmit coil 64 is driven by current via cable 74 from console 34 to generate a magnetic field in the axial direction (Z-axis according to FIGS. 3 and 4). This field is received by coils 66, 68 and 70, which are fixed at different radial locations such that these coils emit electrical signals in response to the magnetic field generated by coil 64. The signals are conveyed by cable 74 to the processor 36 (FIG. 1), which uses them to measure the axial displacement and angular deflection of joint 54.

One or more of the above coils, as well as additional coils (such as coils 72 and 73) oriented in the X and Y directions, are typically also used to output signals in response to magnetic fields generated by external field generators, and thus serve as position sensing coils for the catheter tip.

With this type of magnetic field position and force measurement system 20, it is important to detect the field distortion caused by metal objects located within the magnetic fields especially those near the distal end of catheter 30 in order to avoid coils 66, 68, 70, 72 and 73 outputting incorrect signals which ultimately lead to erroneous measurements/readings of force information or SPI. This problem of SPI is addressed by all of the embodiments of the present invention detailed throughout this disclosure, for example, those embodiments of FIG. 4, FIG. 5, FIG. 6 and FIG. 7.

Accordingly, when a metal object 80 is brought into proximity with distal tip 52, it will distort the magnetic field generated by transmit coil 64 and may, as a result, introduce error into the measurements of displacement, and deflection. This situation of SPI, in which metal object 80 (in this example, another catheter 80) comes close to tip 52, is illustrated in FIG. 4. It is important to detect the field distortion in order to avoid outputting incorrect readings of force.

The parasitic effect of metal object 80 near tip 52 causes the axial field sensed by coils 66, 68 and 70 to decrease sharply. This decrease has a very strong dependence on the distance of the metal object from the tip. When the metal object is very close to the tip, the signals received from coils 66, 68 and 70 will be indicative of a "negative force," i.e., they will be lower than the signals received from the coils in the rest position of joint 54, as though tip 52 were being pulled away from insertion tube 50. This situation is unlikely to be encountered in reality. And thus, constitutes an accurate predictor of the presence of metal object 80 near tip 52 of the catheter 30.

Figure 5:
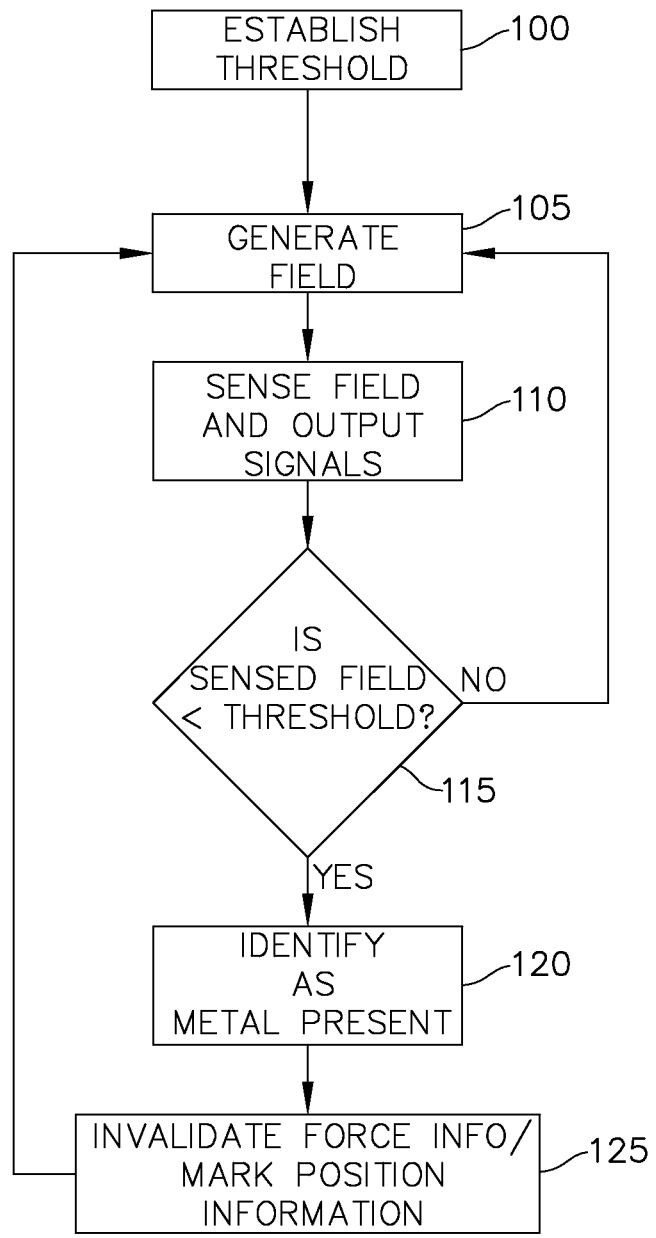
FIG. 5 is a schematic, flow chart of a method for detecting the presence of the metal object of FIG. 4 using the catheter-based medical system of FIG. 1 and the catheter of FIGS. 2, 3 and 4, in accordance with an embodiment of the present invention.

Accordingly, as schematically illustrated in FIG. 5, the method according to the present invention is to establish a threshold field value for system 20 (FIG. 1) while catheter 30 is in its rest position (without axial displacement or angular deflection at its distal end 52 and joint 54) based on the strong signals output by coils 66, 68 and 70 as described previously above. The threshold field value or strength is set as step 100. This threshold field value step 100 is conducted as part of the calibration of the system 20, i.e. prior to use of the catheter 30 on patient 24, wherein the threshold field value 100 is stored in the software of processor 36 of system 20.

Once the threshold field value is set 100, system 20 is ready for use and a magnetic field is generated by magnetic field generator coil 64 (FIGS. 3 and 4), as described above, in step 105. This generated magnetic field 105 is sensed by coils 66, 68 and 70 wherein each respective coil provides a signal output in step 110 based on the strength of the magnetic field from coil 64.

In step 115, processor 36 (FIG. 1) compares the magnetic field 105 sensed by coils 66, 68 and 70 to the threshold field value 100 (based on the signals output by coils 66, 68 and 70). The logic program in software of processor 36 compares the sensed magnetic field value 110 to the threshold field value 100. If the sensed magnetic field value 110 to the threshold field value 100 is at or above threshold field value 100, system 20 continues to operate under normal operating conditions thereby continuing normal cycle of operations with continue generation of magnetic field 105 at magnetic field generator coil 64 with all steps 105, 110, 115 repeated in cycle.

However, in accordance with the present invention, in step 115, if the sensed magnetic field value 110 is below the threshold field value 100, due to coils 66, 68 and 70 providing output signals that are below the pre-established threshold field value 100, the processor 36 identifies SPI, i.e. the force measurement as being influenced by the presence of metal 80 (FIG. 4) in step 120.

Processor 36 then determines that the there is indeed SPI present and that the force measurement readings are invalid in step 125 (due to the disturbance of the magnetic field from generator coil 64). When this sort of field disturbance is detected due to SPI, the processor 36 marks the position coordinate information as suspicious on the display 42). Step 125 optionally includes both a visual indication or indicia depicted in real time on an electro-anatomical map, for example, on display 42 as well as an audible warning or alarm and/or distinct tactile feedback to the operator 26 and steps 105, 110, 115 are repeated in cycle.

As mentioned above, this threshold field value is typically chosen to correspond to zero force on the catheter tip 52 (established in step 100 as part of the calibration and/or start-up procedure), so that sub-threshold readings in step 115 correspond to negative force and automatically identified as metal interference due to presence of metal 80 near tip 52.

Moreover, although coil 64 normally generates only axial field components (along the Z-axis) in the near field, the parasitic effect of a metal object 80 (FIG. 4) near the distal end and/or tip 52 will typically generate radial (X and/or Y axis) components at the driving frequency of coil 64. The amplitude of these parasitic orthogonal field components (X-axis and Y-axis components in this example) has a strong dependence on the distance of the metal object 80 from the distal end of catheter 30. Thus, when the metal object is close to the distal end, the signals received from coils 72, 73 at the driving frequency of coil 64 will increase resulting in SPI.

Figure 6:
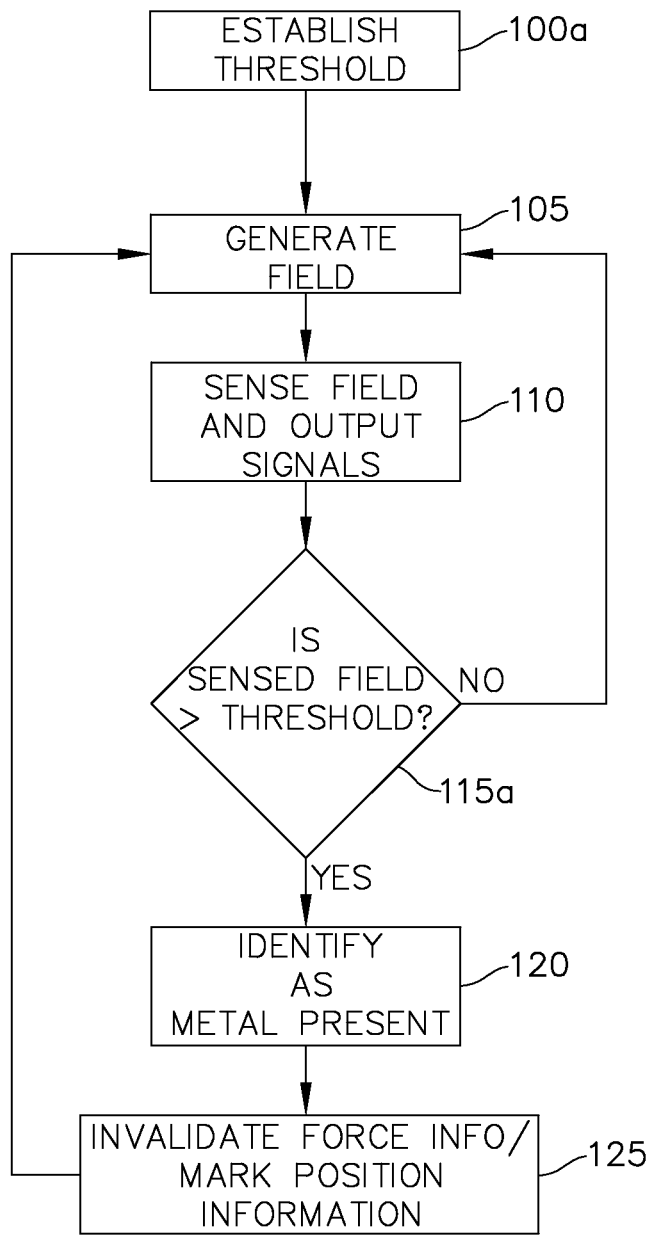
FIG. 6 is a schematic, flow chart of an alternative embodiment of a method for detecting the presence of the metal object of FIG. 4 using the catheter-based medical system of FIG. 1 and the catheter of FIGS. 2, 3 and 4, in accordance with an alternative embodiment of the present invention.

Therefore, when a metal object 80 is present near distal end of catheter 30, another alternative embodiment of the present invention, as best illustrated in FIG. 6, is also used to detect the presence of the metal object 80 and account for SPI and correct readings and measurements of force that may be skewed or erroneous due to the SPI.

In accordance with a further embodiment of the present invention as best illustrated in FIG. 4 and FIG. 6, in order to distinguish between authentic force measurements and distorted ones due to SPI, the present invention utilizes X and Y coils, (the coils 72 and 73 respectively in FIG. 4) Although the X and Y coils (72 and 73) are used for the magnetic position/location information determination, they also receive the force signal although with less sensitivity than the coils 66, 68 and 70 (also referred to as coils S1, S2 and S3 for purposes of the algorithm and calculations below).

All five measurements (from coils S1-S2-S3 and X-Y) relate linearly to the force vector. Thus, there is linear relation between the S1-S2-S3 and the X-Y readings from coils 66-68-70 and coils 72-73 respectively. Because of the different orientation between the X-Y coils (72, 73) and the S1-S2-S3 coils (66, 68, 70), the distortion in the magnetic field caused by a ferromagnetic material 80, causes a different distortion in the X-Y coils (72, 73) as opposed to S1-S2-S3 coils (66, 68, 70), and therefore the relation between the S1-S2-S3 and X-Y signal readings is altered in a measurable manner. This effect enables the present invention to distinguish between a valid force measurement and a distorted force measurement.

The regular correlation between S1-S2-S3 readings (from coils 66, 68, 70) to X-Y readings (72, 73), which is related to valid forces, can be expressed by the following linear relation:

$$\begin{bmatrix} \hat{X}_{Force} \\ \hat{Y}_{Force} \end{bmatrix} = T_{Matrix} \cdot \begin{bmatrix} S_1 \\ S_2 \\ S_3 \end{bmatrix}$$

The SPI-Force Distortion Measure parameter is based on the difference between the expected X-Y measurement and the measured X-Y according to the algorithm of the present invention:

$$SPI = \sqrt{(\hat{X}_{Force} - X_{Force})^2 + (\hat{Y}_{Force} - Y_{Force})^2}$$

The method according to this alternative embodiment of the present invention as best illustrated in FIG. 6 for addressing SPI is to establish a threshold field value 100a for system 20 (FIG. 1) while catheter 30 is in its rest position (without axial displacement or angular deflection at its distal end (includes tip 52 and joint 54) based on the strong signals output by coils 66, 68 and 70 (as well as base line signal from coils 72, 73) as described previously above. The threshold field value or strength is set for system 20 in step 100a. This threshold field value step 100a is conducted as part of the calibration of the system 20, i.e. prior to use of the catheter 30 on patient 24, wherein the threshold field value 100a is stored in the software of processor 36 of system 20.

Once the threshold field value 100a is set, system 20 is ready for use and a magnetic field is generated by magnetic field generator coil 64 (FIGS. 3 and 4), as described above, in step 105. This generated magnetic field 105 is sensed by coils 66, 68 and 70 and coils 72, 73 wherein each respective coil provides a signal output in step 110 based on the strength of the magnetic field from transmit coil 64.

In step 115a, processor 36 (FIG. 1) compares the magnetic field 105 sensed by coils 66, 68 and 70 to the threshold field value 100a (based on the signals output by coils 66, 68 and 70). The logic program in software of processor 36 compares the sensed magnetic field value 110 to the threshold field value 100a using the algorithm address previously above. If the sensed magnetic field value 110 is at or below the threshold field value 100a, system 20 continues to operate under normal operating conditions thereby continuing normal cycle of operations with continue generation of magnetic field 105 at magnetic field generator coil 64 with all steps 105, 110, 115a repeated in cycle.

However, in step 115a, when coil 72 or coil 73, i.e. the corresponding Y-direction coil and/or X-direction coil, gives an output at the driving frequency of coil 64 that is above, i.e. greater than, the given threshold 100a, the processor 36 determines and identifies that magnetic interference is present—which is likely being caused by another device having metal components such as device 80 (FIG. 4) located near distal end of catheter 30.

Since coil 64 normally generates only axial field components along the Z-axis in the near field, the parasitic effect of metal object 80 near distal end of catheter 30 will typically generate radial field components along the X-axis and/or Y-axis at the driving frequency of coil 64. The amplitude of these parasitic orthogonal or radial field components has a strong dependence on the distance of the metal object 80 from the distal end of catheter 30. Thus, when the metal object 80 is close to the catheter 30, the signals received from X-axis coils and Y-axis coils (for example coils 68 and 70 and coil 72, designated as the position sensing coil in this example), as well as coils 72 and 73, at the driving frequency of transmit coil 64 will increase in a non-consistent way (relative to the expected change received from the calibration process).

Thus, in accordance with the present invention, in step 115a, if the sensed magnetic field value 110 is greater than the threshold field value 100a, due to coils 66, 68, 70 and 72, 73 providing output signals that are above the pre-established threshold field value 100a, in step 120, the processor 36 automatically identifies that metal 80 is present and that the present position information (the six dimensional position and orientation coordinate information determined based on position signals received from the coil(s) designated as magnetic position sensors, such as coil 72 in this example, as being a position coordinate influenced by the presence of metal 80 (FIG. 4) in step 125.

In this situation, processor 36 determines that the present force readings are invalid in step 125 (due to the disturbance of the magnetic field from generator coil 64). When this sort of field disturbance is detected, the processor 36 optionally invalidates the position coordinate reading/information (or at least marks the position coordinate information as suspicious on the display 42). Step 125 optionally includes both a visual indication or indicia depicted in real time on an electro-anatomical map, for example, on display 42 as well as an audible warning or alarm and/or distinct tactile feedback to the operator 26 and steps 105, 110, 115a are repeated in cycle until the metal object is cleared from the magnetic field or accounted for with adjustment calculations to the force measurement readings.

As mentioned above, this threshold field value 100a is typically chosen to correspond to zero force on the catheter tip 52 (established in step 100a as part of the calibration and/or start-up procedure), so that above-threshold readings from axial component signals in the X-axis direction and Y-axis direction in step 115a are automatically identified as metal interference due to presence of metal 80 near distal end of catheter 30.

Alternatively or additionally, when the interference from presence of metal 80 is not too extreme, i.e. signal outputs slightly above threshold values 100a, the processor 36 can attempt to correct the force readings to compensate for the metal interference (SPI).

In another method according to yet another alternative embodiment of the present invention for addressing SPI, the parasitic effect of a metal object 80 near distal end of catheter 30, such as near the tip 52, causes a change in the mutual inductance between coils 66, 68 and 70 in the magnetic field generation position tracking system 20 (FIGS. 1-4). This change in mutual inductance has a strong dependence on the distance of the metal object 80 from the distal end of catheter 30.

Figure 7:
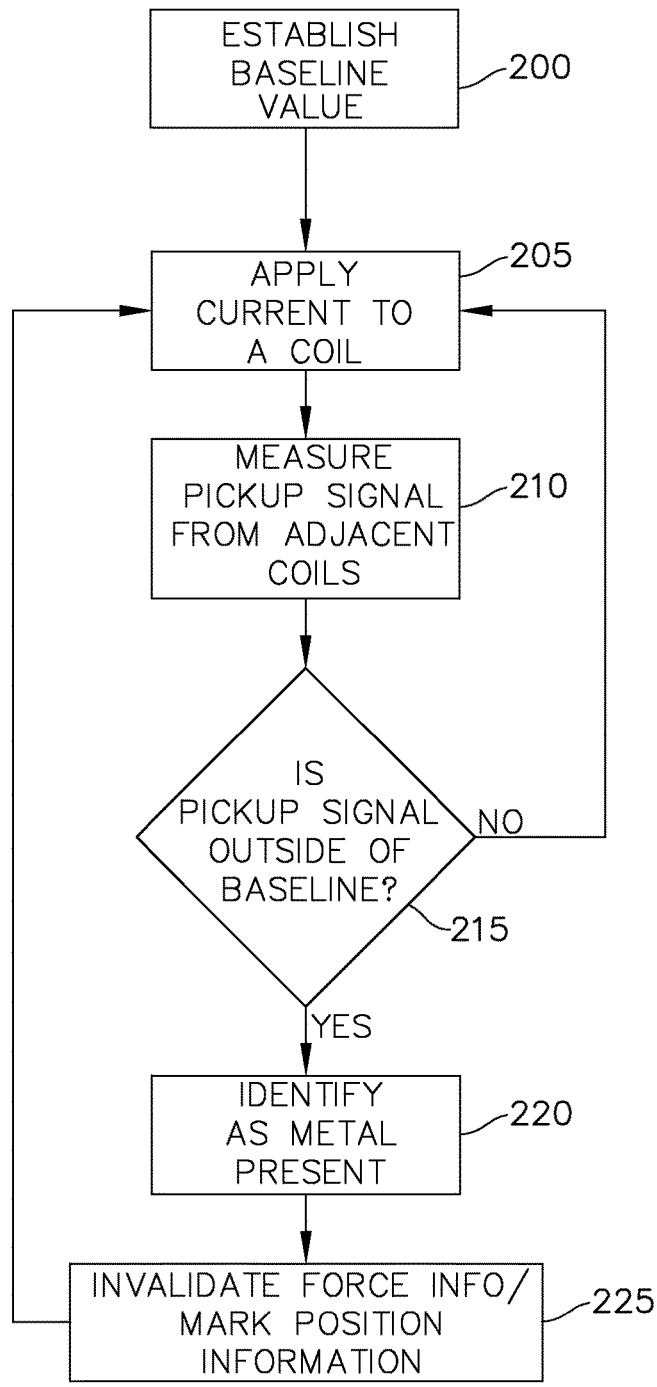
FIG. 7 is a schematic, flow chart of another alternative embodiment of a method for detecting the presence of the metal object of FIG. 4 using the catheter-based medical system of FIG. 1 and the catheter of FIGS. 2, 3, and 4 in accordance with another alternative embodiment of the present invention.

Accordingly, in this alternative embodiment of the present invention, as best illustrated in FIG. 7, the system 20 (FIG. 1) provides for a method (FIG. 7) wherein an initial baseline value for the mutual inductance detected between coils 66, 68 and 70 of catheter 30 is pre-determined or pre-established at time of manufacture or just prior to use on a patient 24 and stored in the logic of processor 36. This mutual inductance baseline value is an expected range (including an acceptable deviation factor +/−) of inductance measured amongst the coils 66, 68 and 70 when one of the coils has current applied directly thereto without any metal being present near the catheter 30. Thus, this is a calibration step 200 for determining the mutual inductance baseline value of the coils 66, 68 and 70 in the absence of any metal object.

The mutual inductance coils 66, 68 and 70 is measured, for example, by applying or injecting a current at a certain, known frequency through one of these coils, for example coil 66, and measuring the signals that are induced in the other remainder coils, for example adjacent coils 68 and 70, as a result. Under normal circumstances, i.e. in the calibration stage 200, these pickup signals should be invariant. A change in these pickup signals indicates that the mutual inductance has changed, presumably due to a metal object 80 located near the distal end of catheter 30.

Therefore, in this embodiment of the present invention, a current at a predetermined frequency is periodically applied or injected into one or more of coils 66, 68 and 70 in step 205, and the resulting pickup signal in the other remainder coil(s), i.e. the non-injected coils, are measured 210. As mentioned above, the baseline pickup value is measured under conditions without metal interference in step 200 and pre-stored in processor 36 which allows processor 36 in step 215 to compare the pickup value (based on the measured pickup signals from the non-injected coils) to the baseline value range (which includes the acceptable deviation factor expected in an environment without metal being present) and if the pickup signal value subsequently deviates from the baseline value by more than the permitted amount (the acceptable range), the processor 36 in step 220 makes a determination and identifies SPI, i.e. that the magnetic field has been disturbed by a nearby metal object 80.

When this sort of field disturbance is detected, the processor 36 in step 225 typically invalidates (or at least marks as suspicious) the force measurements made by coils 66, 68 and 70. The user 26 then has the option to seek out and remove the source of the metal object interference and/or take evasive measures to account for the presence of such a metal object 80.

In this situation, processor 36 determines that the present force measurement readings are invalid in step 225 (due to the mutual inductance measurements being out-of-bounds, i.e. outside baseline value 200) and when this sort of field disturbance is detected, the processor 36 invalidates the Force reading/information. Step 225 optionally includes both a visual indication or indicia depicted in real time on an electro-anatomical map, for example, on display 42 as well as an audible warning or alarm and/or distinct tactile feedback to the operator 26 and steps 205, 210, 215 are repeated in cycle until the metal object is cleared from the magnetic field or accounted for with adjustment calculations to the force measurement readings.

In step 215, if the pickup signal value is within the established baseline value 200, the process continues in cycle, i.e. steps 205, 210 and 215 are repeated in cycle and magnetic field position sensing system continues to operate in this manner providing accurate six-dimensional position and orientation coordinate information along with the accurate force measurement capability of catheter 30 thereby eliminating the effects from SPI.

It will thus be appreciated that the embodiments described above are cited by way of example, and that the present invention is not limited to what has been particularly shown and described hereinabove. Rather, the scope of the present invention includes both combinations and subcombinations of the various features described hereinabove, as well as variations and modifications thereof which would occur to persons skilled in the art upon reading the foregoing description and which are not disclosed in the prior art.

We claim:

1. Apparatus for detecting metal objects during a medical procedure comprising:
    a probe, which comprises: an insertion tube, having a longitudinal axis and having a distal end, the probe configured to generate X-Y position signals indicative of a position of the distal end of the probe, and to generate force signals indicative of force exerted on the distal end of the probe;
        wherein the probe is a catheter adapted for insertion into a patient;
    a distal tip, which is disposed at the distal end of the insertion tube and is configured to be brought into contact with tissue of the body;
    at least one X-Y sensor disposed within said probe, said at least one X-Y sensor providing the X-Y position signals indicative of the position of the distal end of the probe;
        wherein said at least one X-Y sensor is oriented for receiving magnetic fields along a respective X axis or Y axis;
    a joint, which couples the distal tip to the distal end of the insertion tube;
    a joint sensor, contained within the probe, for sensing a position of the distal tip relative to the distal end of the insertion tube, the joint sensor comprising a first subassembly and a second subassembly, which are disposed within the probe on opposite, respective sides of the joint and comprising magnetic transducers for generating the signals indicative of force exerted on the distal end of the probe;
        wherein the first subassembly comprises a field coil, the field coil being configured to generate a magnetic field along an axial Z-axis, the magnetic field having a first driving frequency when driven by an electrical current;
        wherein the second subassembly comprises a plurality of receiving transducers fixed at different radial locations within the probe, the receiving transducers adapted to emit respective electric signals in response to said magnetic field along the axial Z-axis generated by the field coil;
        wherein the electrical signals emitted by respective receiving transducers are force signals, and vary in response to movement of the distal tip with respect to the distal end of the insertion tube;
    a display for displaying an electroanatomical map; and
    a processor for generating the electroanatomical map based on the X-Y position signals from the at least one X-Y sensor of the probe, and for determining a force measurement based on the force signals from the second subassembly of the joint sensor, the processor also being adapted to apply said current to the field coil, and to detect changes in the position of the distal tip with respect to the distal end of the insertion tube based on varying electrical signals received from the receiving transducers;
    the processor having a threshold field value stored therein, the threshold field value being based on signals output by the field coil;
    the processor being adapted to compare a first driving frequency component of the X-Y position signal, if any, with the threshold field value, and to identify a presence of a metal object near the catheter and within the patient when the first driving frequency component of the X-Y position signal is greater than the threshold field value;

when the presence of the metal object is identified, marking position information for the metal object using a visual indicator marked in real time on the electroanatomical map on the display and performing one of correcting the determined force measurement, and invalidating the determined force measurement, wherein the X-Y sensor comprises a first X-Y sensor coil and a second X-Y sensor coil, wherein the first X-Y sensor coil and the second X-Y sensor coil are adapted and oriented to receive force signals, wherein the coils of the second subassembly and the coils of the X-Y sensor are adapted and oriented so that all measurements received from the coils of the second subassembly and the coils of the X-Y sensor relate linearly to a force vector, wherein the coils of the second subassembly and the coils of the X-Y sensor are adapted and oriented so that there is linear relation between readings from the coils of the second subassembly and readings from the coils of the X-Y sensor, wherein the coils of the second subassembly and the coils of the X-Y sensor are oriented relative to one another such that a distortion in the magnetic field caused by the metal object, causes a different distortion in the coils of the second subassembly than in the coils of the X-Y sensor, wherein the relation between second subassembly signal readings and X-Y sensor readings is measurably altered, and wherein the processor causes an audible alarm accompanied by distinct tactile feedback, upon identifying the presence of the metal object near the distal end of the probe.

2. The apparatus according to claim 1, wherein said at least one X-Y sensor within the probe comprises an X sensor oriented along the X axis with respect to the probe, and a Y sensor oriented along the Y axis with respect to the probe.

3. The apparatus according to claim 2, and comprising a magnetic field generator, for generating a further magnetic field in a vicinity of the body, and the X-Y sensor in the probe for generating a position signal in response to the further magnetic field, wherein the processor is coupled to receive and process the position signal in order to compute position coordinates of the probe relative to a frame of reference that is separate from the probe.

4. The apparatus according to claim 3, wherein the joint sensor comprises at least one of the magnetic transducers in one of the first subassembly and the second subassembly.

5. The apparatus according to claim 4, wherein the magnetic transducers comprise field coils, and wherein the first subassembly comprises a first field coil having a first coil axis parallel to the longitudinal axis of the insertion tube, and wherein the second subassembly comprises two or more second field coils in different, respective radial locations within a section of the probe that is spaced apart axially from the first subassembly.

6. The apparatus according to claim 3, further comprising the display and wherein the processor identifies the presence of the metal object near the distal end of the probe through indicia provided on the display.

7. The apparatus according to claim 1, wherein the changes in the position of the distal tip detected by the processor comprise an axial displacement of the distal tip and a deflection of the distal tip relative to the distal end of the insertion tube.

8. The apparatus according to claim 1, wherein the joint comprises a resilient member, which is configured to deform in response to pressure exerted on the distal tip.

9. A method for detecting metal objects during an invasive medical procedure, comprising:

providing an apparatus, the apparatus comprising:
 a probe configured to generate X-Y position signals indicative of a position of the distal end of the probe, and force signals indicative of force exerted on the distal end of the probe, the probe comprising:
  an insertion tube having a longitudinal axis and having a distal end;
  a distal tip disposed at the distal end of the insertion tube;
  at least one X-Y sensor within the probe, said at least one X-Y sensor providing the X-Y position signals indicative of the position of the distal end of the probe, wherein said at least one X-Y sensor is oriented for receiving magnetic fields along a respective X axis or Y axis;
  a joint, which couples the distal tip to the distal end of the insertion tube;
  a joint sensor within the probe for sensing a position of the distal tip relative to the distal end of the insertion tube, the joint sensor comprising a first subassembly and a second subassembly, which are disposed within the probe on opposite, respective sides of the joint and comprising magnetic transducers for generating the signals indicative of force exerted on the distal end of the probe;
   the first subassembly comprising a field coil, the field coil being configured to generate a magnetic field along an axial Z-axis, the magnetic field having a first driving frequency when driven by an electrical current;
   the second subassembly comprising a plurality of receiving transducers fixed at different radial locations within the probe, the receiving transducers adapted to emit respective electric signals in response to said Z-axis magnetic field generated by the field coil;
   wherein the electrical signals emitted by respective receiving transducers are force signals, and vary in response to movement of the distal tip with respect to the distal end of the insertion tube;
 a display for displaying an electroanatomical map; and
 a processor adapted for generating the electroanatomical map based on the X-Y position signals from the at least one X-Y sensor of the probe, and for determining a force measurement based on the force signals from the second subassembly of the joint sensor,
  the processor having a threshold field value stored therein, the threshold field value being based on signals output by the field coil;

the method comprising:
inserting the probe into a patient, and moving the probe to a first position within the patient in contact with a tissue surface;
applying a current to the field coil of the first assembly, and the field coil generating a magnetic field having a first driving frequency along an axial Z-axis;

the receiving transducers of the second assembly receiving the magnetic field generated by the first assembly, and the receiving transducers generating respective electric force signals;

the processor detecting at least one of a compression and a deflection of the distal tip based on the electrical force signals from the receiving transducers;

the processor receiving X-Y position signals from the at least one X-Y sensor, determining and displaying on the electroanatomical map a first position of the distal end of the probe based on the X-Y position signals; and thereafter:

moving the probe to a second position within the patient in a vicinity of a metal object, with the field coil generating the magnetic field having the first driving frequency along the axial Z-axis;

the metal object interfering with the magnetic field having the first driving frequency along the axial Z-axis;

the at least one X-Y sensor receiving the magnetic field at the first driving frequency and in response thereto generating an X-Y position signal having a first driving frequency component;

using the processor, comparing the first driving frequency component of the X-Y position signal to the threshold field value, determining that the first driving frequency component of the X-Y position signal is greater than the threshold field value and, in response to said determination, marking the electroanatomical map with a visual indicator indicating the metal object, and initiating an audible alarm accompanied by distinct tactile feedback upon identifying the presence of the metal object near the distal end of the probe based on said determination that the first driving frequency component of the X-Y position signal is greater than the threshold field value, wherein the X-Y sensor comprises a first X-Y sensor coil and a second X-Y sensor coil, wherein the first X-Y sensor coil and the second X-Y sensor coil are adapted and oriented to receive force signals, wherein the coils of the second subassembly and the coils of the X-Y sensor are adapted and oriented so that all measurements received from the coils of the second subassembly and the coils of the X-Y sensor relate linearly to a force vector, wherein the coils of the second subassembly and the coils of the X-Y sensor are adapted and oriented so that there is linear relation between readings from the coils of the second subassembly and readings from the coils of the X-Y sensor, wherein the coils of the second subassembly and the coils of the X-Y sensor are oriented relative to one another such that a distortion in the magnetic field caused by the metal object, causes a different distortion in the coils of the second subassembly than in the coils of the X-Y sensor, and wherein the relation between second subassembly signal readings and X-Y sensor readings is measurably altered.

10. The method according to claim 9 wherein said at least one X-Y sensor within the probe comprises an X sensor and a Y sensor;

the method comprising:

at least one of the X sensor and the Y sensor receiving the magnetic field at the first driving frequency generated by the field coil of the first assembly and providing said X-Y position signal; and using the processor, comparing the first driving frequency component of the X-Y position signal to the threshold field value, determining that the first driving frequency component of the X-Y position signal is greater than the threshold field value and, in response to said determination, marking the electroanatomical map with the visual indicator indicating the metal object.

11. The method according to claim 10, wherein detecting the changes in the position of the distal tip comprise detecting at least one of an axial displacement of the distal tip and a deflection of the distal tip relative to the distal end of the insertion tube.

12. The method according to claim 9, further comprising displaying indicia on the display upon identifying the presence of the metal object near the distal end of the probe.

13. The method according to claim 9, further comprising determining the position of the distal tip relative to the distal end of the insertion tube based on position coordinates.

14. The method according to claim 13, wherein the position coordinates comprise X, Y, and Z directions and pitch, yaw and roll orientations.

15. The method according to claim 9, wherein the joint comprises a resilient member and the joint deforms in response to pressure exerted on the distal tip.

16. A method for detecting metal objects during an invasive medical procedure, comprising:

providing an apparatus, the apparatus comprising:

a probe configured to generate X-Y position signals indicative of a position of the distal end of the probe, and force signals indicative of force exerted on the distal end of the probe, the probe comprising:

an insertion tube having a longitudinal axis and having a distal end;

a distal tip disposed at the distal end of the insertion tube;

at least one X-Y sensor within the probe, said at least one X-Y sensor providing the X-Y position signals indicative of the position of the distal end of the probe;

a joint, which couples the distal tip to the distal end of the insertion tube;

a joint sensor within the probe for sensing a position of the distal tip relative to the distal end of the insertion tube, the joint sensor comprising a first subassembly and a second subassembly, which are disposed within the probe on opposite, respective sides of the joint and comprising magnetic transducers for generating the signals indicative of force exerted on the distal end of the probe;

the first subassembly comprising a field coil, the field coil being configured to generate a magnetic field having a first driving frequency when driven by an electrical current;

the second subassembly comprising a plurality of receiving transducers within the probe, the receiving transducers adapted to emit respective electric signals in response to said magnetic field generated by the field coil which vary in response to movement of the distal tip with respect to the distal end of the insertion tube; and a processor, the processor having a threshold field value stored therein, the threshold field value being based on signals output by the field coil;

the method comprising:

inserting the probe into a patient, and moving the probe to a first position within the patient in contact with a tissue surface;

the field coil of the first subassembly generating the magnetic field having the first driving frequency;

the metal object interfering with the magnetic field having the first driving frequency;

the at least one X-Y sensor receiving the magnetic field at the first driving frequency and in response thereto generating an X-Y position signal having a first driving frequency component;

using the processor, comparing the first driving frequency component of the X-Y position signal to the threshold field value, determining that the first driving frequency component of the X-Y position signal is greater than the threshold field value and, in response to said determination, identifying a metal object, and initiating an audible alarm accompanied by distinct tactile feedback upon identifying the presence of the metal object near the distal end of the probe based on said determination that the first driving frequency component of the X-Y position signal is greater than the threshold field value, wherein the X-Y sensor comprises a first X-Y sensor coil and a second X-Y sensor coil, wherein the first X-Y sensor coil and the second X-Y sensor coil are adapted and oriented to receive force signals, wherein the coils of the second subassembly and the coils of the X-Y sensor are adapted and oriented so that all measurements received from the coils of the second subassembly and the coils of the X-Y sensor relate linearly to a force vector, wherein the coils of the second subassembly and the coils of the X-Y sensor are adapted and oriented so that there is linear relation between readings from the coils of the second subassembly and readings from the coils of the X-Y sensor, wherein the coils of the second subassembly and the coils of the X-Y sensor are oriented relative to one another such that a distortion in the magnetic field caused by the metal object, causes a different distortion in the coils of the second subassembly than in the coils of the X-Y sensor, and wherein the relation between second subassembly signal readings and X-Y sensor readings is measurably altered.

* * * * *